United States Patent [19]

De Vadder et al.

[11] Patent Number: 4,631,965
[45] Date of Patent: Dec. 30, 1986

[54] ACOUSTIC HOLOGRAPHY PROCESS AND APPARATUS USING A SPACE-LIMITED ULTRASONIC BEAM

[75] Inventors: Daniel De Vadder, Verrieres le buisson; Robert Saglio, Antony, both of France

[73] Assignee: COMMISSARIAT a l'Energie Atomique, Paris, France

[21] Appl. No.: 602,367

[22] Filed: Apr. 20, 1984

[30] Foreign Application Priority Data

Apr. 29, 1983 [FR] France .................................. 83 07166

[51] Int. Cl.⁴ .............................................. G01N 29/04
[52] U.S. Cl. ........................................ 73/602; 73/603; 73/625
[58] Field of Search ................... 73/625, 626, 602, 603

[56] References Cited

U.S. PATENT DOCUMENTS

| | | | |
|---|---|---|---|
| 4,145,931 | 3/1979 | Tanarell | 73/626 |
| 4,170,142 | 10/1979 | Posakany et al. | 73/626 |
| 4,254,662 | 3/1981 | Kuroda et al. | 73/626 |
| 4,319,489 | 3/1982 | Yamaguchi et al. | 73/626 |
| 4,437,176 | 3/1984 | Mack | 367/56 |
| 4,448,076 | 5/1984 | Heelsbergen | 73/626 |

FOREIGN PATENT DOCUMENTS 2923687 4/1981 Fed. Rep. of Germany .

*Primary Examiner*—Howard A. Birmiel
*Attorney, Agent, or Firm*—Oblon, Fisher, Spivak, McClelland & Maier

[57] ABSTRACT

The fault-containing area to be inspected is insonified by means of an ultrasonic transducer with a space-limited beam which is displaced in stepwise manner, the signals coming from the successively insonified areas being detected by several receivers, the phases and amplitudes of the signals being determined and the reconstitution of the area to be inspected performed. There is a main image of the fault and also parasitic images thereof. The number of receivers is chosen in such a way that the distance between the parasitic images and the main image exceeds the width of the area insonified by the transmitter and the reconstitution is only carried out in the insonified areas having given rise to a signal in order to eliminate the parasitic images. Application to the non-destructive inspection of mechanical parts.

8 Claims, 10 Drawing Figures

ACOUSTIC HOLOGRAPHY PROCESS AND APPARATUS USING A SPACE-LIMITED ULTRASONIC BEAM

BACKGROUND OF THE INVENTION

The present invention relates to an acoustic holography process and apparatus using a space-limited ultrasonic beam. It is used more particularly in the non-destructive testing of mechanical parts.

The principle of acoustic holography will be described relative to FIG. 1. By means of an ultrasonic transducer 2 able to transmit plane waves, one or more faults, i.e. one or more material breaks or interruptions in an object are insonified. In other words, the fault or faults are excited by an ultrasonic beam transmitted by the transducer and which is consequently called the "insonification beam". FIG. 1 shows the direction 4 of the ultrasonic beam, as well as the wave planes 5 perpendicular to said direction. The beam 6, diffracted and reflected by the fault or faults 3 is analyzed at several points 7, aligned in an examination plane 8, which can differ from the transmission plane 9 from which the insonification beam has been transmitted, by comparison with a reference beam similar to the insonification beam. This makes it possible to determine for each of the points 7 of examination plane 8, the phase and amplitude of the signal received at this point. The reconstitution or reconstruction of the fault or faults 3 is then carried out by calculating or reconstituting by any appropriate means, the sound pressure in the examined volume 10 containing the fault or faults 3. This pressure is produced by a transmitter located in examination plane 8 and which will have the predetermined amplitude and phase characteristics.

An acoustic holography process and apparatus are known and will be described with reference to FIGS. 2 and 3. Moreover, only acoustic holography in one plane, i.e. holography of planar sections of objects, is envisaged in FIGS. 2 and 3, the examination of a volume being obtained by successively effecting holograms in parallel section planes of said volume. FIG. 2 shows a planar section of a mechanical part 11, having a fault 12, the section plane coinciding with the plane of FIG. 2. The known apparatus, used for the acoustic holography of the fault, comprises a transmitter-receiver ultrasonic transducer 13, whose divergence angle $\alpha$ is very large and which is linearly displaceable on surface 14 of part 11, said surface being assumed flat. The transducer 13 occupies M successive positions $P_1, P_2, \ldots, P_M$, which are separated from one another by a distance at the most equal to the transmission wavelength of the transducer. The occupation of M successive positions by transducer 13 enables the acoustic beam transmitted by the latter to insonify the fault in several orientations, within the aperture L of the beam, which is equal to the distance separating the two extreme positions $P_1$ and $P_M$ of transducer 13. For each of the M positions, the signal is transmitted by transducer 13, functioning as a transmitter, the echo signal reflected by the fault 12 being intercepted by said transducer then acting as a receiver and the phase and the amplitude of the echo signal are evaluated. Thus, it is the real part and the imaginary part of the echo signal (considered in complex form) which, in an equivalent manner, are evaluated. Thus, the amplitude-phase acoustic distribution on the surface 14 of part 11 is known. On the basis of these amplitudes and phases, the corresponding sound pressure is calculated (FIG. 3) on a circle, whose centre is the point O located on surface 14 of part 11 and in the centre of aperture L of the transducer and whose radius R is equal to the distance corresponding to the acoustic path necessary for reaching the fault or faults 12. On this circle, the sound pressure is at a maximum at the point or points forming part of the fault or faults 12.

The known process and apparatus described hereinbefore make it possible to obtain, substantially in real time, an evaluation of the size of the faults present in mechanical parts in a given direction, by means of a mechanical arrangement and relatively simple mathematical algorithms, but suffer from numerous disadvantages, the most important of which are given hereinafter.

Firstly, this process and this apparatus only give a very low signal/noise ratio. Thus, the ultrasonic beam transmitted by the transducer is very divergent and the acoustic pressure is proportional to $z^{-2}\alpha^{-1}$, z being the distance between the transducer and the fault and $\alpha$ the solid divergence angle of said beam. Thus, the amplitude of the signal received by the transducer is a very rapidly decreasing function of the distance z and the solid angle $\alpha$, whilst the noise which is linked with the structure is a rising function of the solid angle $\alpha$.

Furthermore, this process and apparatus do not make it possible to obtain a good reconstitution of large flat faults or only give reconstitutions, whose quality is highly dependendent on the orientation of the studied faults. Thus, in the case of a large flat fault 15 in part 11, even if for a position $P_i$ of transducer 13 intermediate between the extreme positions $P_1$ and $P_M$, the mean insonification direction is perpendicular to fault 15 and encounters the latter in its centre (FIG. 4b), so that a large echo is received by this transducer, whilst the insonification of the fault on its edges, corresponding to the extreme transducer positions $P_1$ and $P_M$, gives a substantially zero echo signal on the transducer, said echo signal then being transmitted outside the insonification beam (FIGS. 4A and 4C).

SUMMARY OF THE INVENTION

The object of the invention is an acoustic holography process and apparatus not suffering from the disadvantages of existing processes and apparatuses, particularly through permitting a considerable improvement to the signal/noise ratio, whilst reducing the sensitivity to the orientation of the investigated faults.

More specifically, the present invention relates to a process for the acoustic holography of an area to be inspected in an object, said area being liable to contain at least one fault, wherein it comprises insonifying the area to be inspected by means of an ultrasonic transmitter producing a space-limited ultrasonic beam, by displacing the transmitter so as to successively insonify M areas, whose bringing together covers the area to be inspected; detecting ultrasonic signals likely to come from the successively insonified areas in response to the ultrasonic beam, by means of several ultrasonic receivers having reciprocal spacings; determining the characteristic values of the detected ultrasonic signals; and reconstituting the area to be inspected by means of said characteristic values, this reconstitution comprising a main image of the fault and optionally secondary images thereof due to the said spacings; wherein the number N of receivers is predetermined in such a way that the distance between each secondary image and the main image exceeds the width of the areas insonified by the transmitter and wherein the reconstitution is only carried out in the insonified areas which have given rise to an ultrasonic signal, so as to eliminate the secondary images from the reconstitution of the area to be inspected.

"Fault" is understood to mean any material break or interruption in the object and comprises e.g. a crack or blister in a mechanical part. The term "characteristic values of the ultrasonic signals" is understood to mean the phase-amplitude pairs corresponding to the said signals, or all the equivalent pairs to those indicated hereinbefore, such as the real and imaginary parts of the signals. Preferably, the space-limited ultrasonic beam is a focused ultrasonic beam. The notion of the focused ultrasonic beam will be explained hereinafter.

The present invention also relates to an apparatus for the acoustic holography of an area to be inspected in an object, said area being liable to contain at least one fault, wherein it comprises an ultrasonic transmitter able to produce a space-limited ultrasonic beam and which serves to insonify the area to be inspected; means for the displacement of the transmitter enabling the latter to successively insonify M areas, whose bringing together covers the area to be inspected; a plurality of ultrasonic receivers having reciprocal spacings and serving to detect the ultrasonic signals liable to come from the successively insonified areas in response to the ultrasonic beam; and means for processing the detected ultrasonic signals for determining the characteristic values of said signals and for effecting a reconstitution of the area to be inspected with the aid of said characteristic values, the reconstitution incorporating a main image of the fault and optionally secondary images of said fault, due to the said spacings; the number N of receivers being predetermined in such a way that the distance between each secondary image and the main image exceeds the width of the areas insonified by the transmitter, the processing means serving to carry out the reconstitution only in the insonified areas which have given rise to an ultrasonic signal so as to eliminate the secondary images from the reconstitution of the area to be inspected.

According to a special embodiment of the apparatus according to the invention, the N receivers are fixed, the displacement means serving to successively position the transmitter in M different positions respectively corresponding to the M zones, each receiver then successively receiving at the most M ultrasonic signals, whilst the processing means serve to summate, for each receiver, these M ultrasonic signals, so as to form N signal sums, and for carrying out the reconstitution of the area to be inspected on the basis of these N sums.

In this case, the receivers can be advantageously designed and arranged in such a way as to have a spatial reception diagram, which envelops the area to be inspected. This makes it possible to still further increase the signal/noise ratio.

According to another special embodiment of the apparatus according to the invention, the N receivers are movable and are rendered rigidly integral with the transmitter, the displacement means serving to position the transmitter in M different positions, corresponding respectively to the M areas and the processing means serve to carry out a reconstitution of the area insonified for each position of the transmitter.

According to an improvement to this special embodiment, the displacement means are translation means, the receivers also being aligned in the direction of said translation and being equidistant of one another in accordance with a given spacing p, whilst the displacement means also displace the assembly constituted by the transmitter and the receivers by successive spacings less than the spacing of the receivers. In the presence of the area insonified by the transmitter, it is possible to considerably increase the number of informations received by the receivers, without essentially modifying the insonified area.

According to an improvement to this special embodiment, the receivers are designed and oriented so as to have a spatial reception diagram, which envelops the area insonified by the transmitter, which makes it possible to increase the signal/noise ratio.

Finally, according to a main feature of the invention, the ultrasonic transmitter is a focused transducer, which may or may not be monolithic. For example, it is possible to use a focusing probe or a strip of piezoelectric transducers, whose focusing is carried out electronically by means of electronic delay lines in a manner known in the art.

BRIEF DESCRIPTION OF THE DRAWINGS

The invention is described in greater detail hereinafter relative to non-limitative embodiments and with reference to the attached drawings, wherein show.

DETAILED DESCRIPTION OF THE PREFERRED EMBODIMENTS

Figure 5:
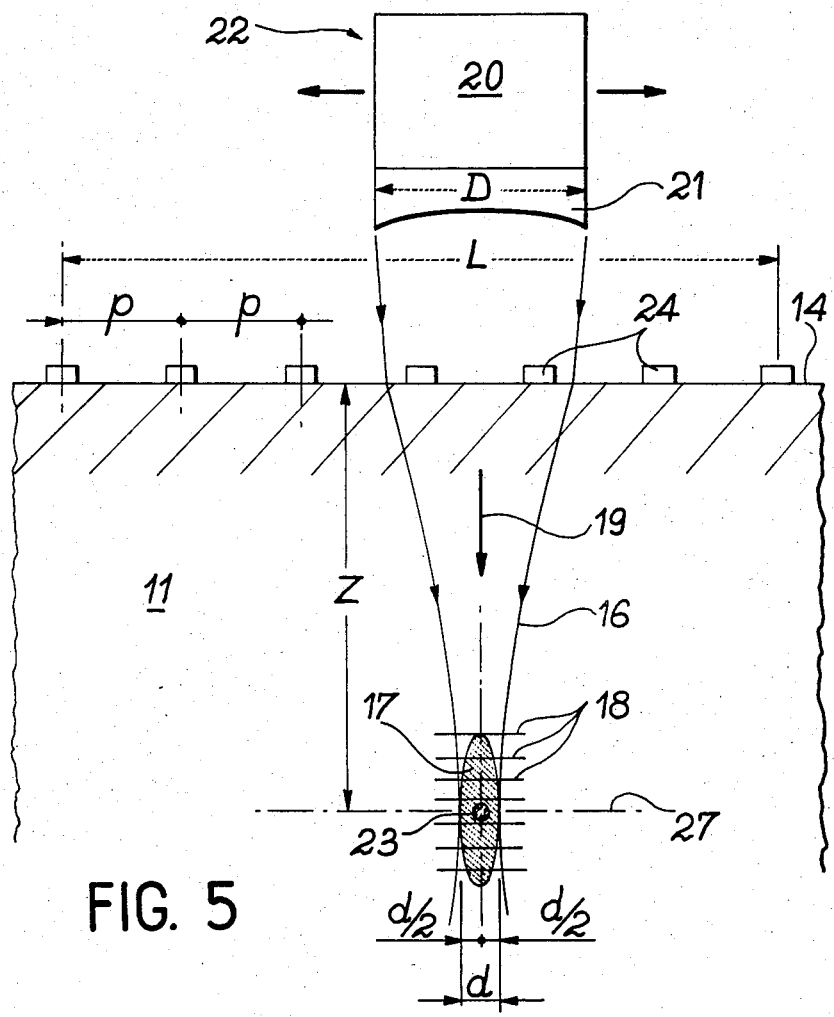
FIG. 5 a diagrammatic view of a focused transducer used in the invention.

FIG. 5 diagrammatically shows a focused ultrasonic beam 16. It is a convergent ultrasonic beam, whose cross-section passes through a minimum and which consequently insonifies a reduced region 17 of the space in the vicinity of said minimum. Moreover, such a focused beam has the following characteristic. Within said region, the wave fronts are planes 18 perpendicular to the propagation direction 19 of the beam. This focused beam can be obtained by exciting a piezoelectric transducer 20 associated with an acoustic focusing lens 21, the assembly 22 constituted by the transducer and the lens forming a focused transducer.

Figure 6:
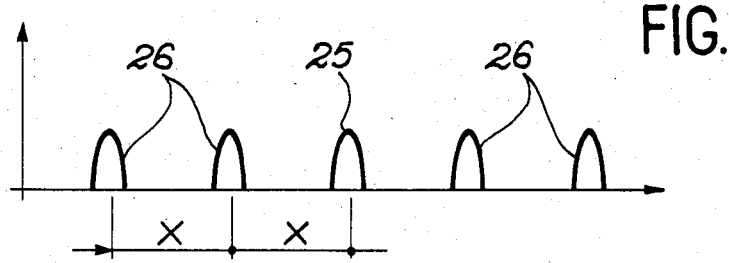
FIG. 6 a diagrammatic view of the secondary images which may be observed in the reconstitution of an object in acoustic holography.

According to the invention, a fault 23 in a part 11 is insonified by a focused ultrasonic beam 16, which is made to occupy several successive positions in order to recreate a homogeneous acoustic field. A finite number N of spaced ultrasonic receivers 24 is used. The reconstitution of the fault 23 leads to the appearance not only of the real image 25 of the fault, or main image, but also the parasitic or secondary images 26 of the fault, which can be seen in FIG. 6, which e.g. shows the reconstitution displayed on an oscilloscope screen.

For receivers 24 aligned in a plane, such as the assumed flat surface 14 of part 11 and which are equidistant of one another in accordance with a spacing p, the images 25 or 26 are aligned and equidistant with a spacing X equal to $\lambda Z/p$, in which $\lambda$ is the wave length of the ultrasonic beam and Z the distance between the plane 14 of the receivers and the reconstitution plane, i.e. a plane 27 parallel to plane 14 of the receivers and intersecting fault 23.

According to the invention, the spacing p between the receivers (which amounts to choosing the number N of receivers for a focused beam with a given aperture L differing slightly from the product N·p) is chosen in such a way that the distance 2X between the two secondary images closest to the main image 25 is more than twice the width d of the region or area 17 insonified by beam 16. In other words, the number N of receivers is chosen in such a way that the distance between each secondary image and the main image exceeds the width d of the insonified area 17.

Moreover, in view of the different successive positions occupied by the ultrasonic beam and consequently the areas successively insonified by said beam, reconstruction or reconstitution is only carried out for the areas which have given rise to an echo, which consequently eliminates any parasitic image from the reconstitution. This can be carried out by means of an electronic computer, starting by determining and then digitizing the real and imaginary parts of the echo signals received by receivers 24. Reconstitution takes place with the aid of the computer. The reconstitution calculation leads to the secondary images corresponding to the insonified areas which have not given rise to any echo. The computer also stores all the insonified areas by marking those which have not given rise to any echo, which enables the computer to eliminate the secondary images from the reconstitition. Preferably, the reconstitution calculation is not carried out in the insonified areas which have not given rise to any echo, which decreases to the same degree the calculation or computing time.

The value of the space X between the images referred to hereinbefore makes it possible to determine the number N of receivers. The condition imposed on spacing X, also given hereinbefore, is as follows:

$$X > d \text{ or } \lambda Z/p > d \quad (1)$$

As N·p is close to L, the inequation (1) becomes:

$$N > Ld \cdot (\lambda Z)^{-1} \quad (2)$$

The present invention uses a focused beam, which insonifies a region of reduced width d and consequently makes it possible on the basis of inequation (2) to only use a small number N of receivers. Distance Z can e.g. be determined by echography.

The lateral resolving power of an acoustic holography apparatus is equal to $2\lambda Z \cdot (Np)^{-1}$. Thus, as the invention uses few ultrasonic receivers, for the same resolving power it is less expensive, easier to operate and consumes less calculating time than the known techniques which require a large number of ultrasonic receivers.

Figure 1:
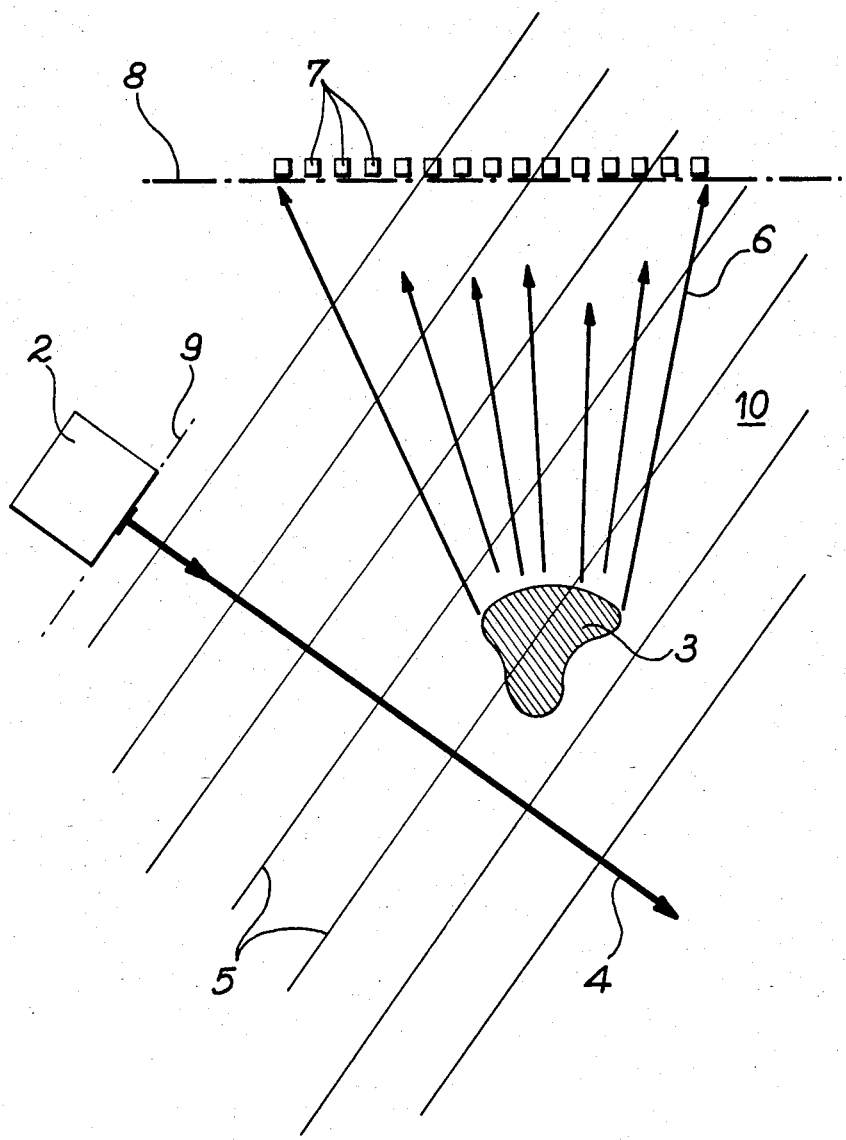
FIG. 1 a diagram for explaining the principle of acoustic holography, already described.
Figure 2:
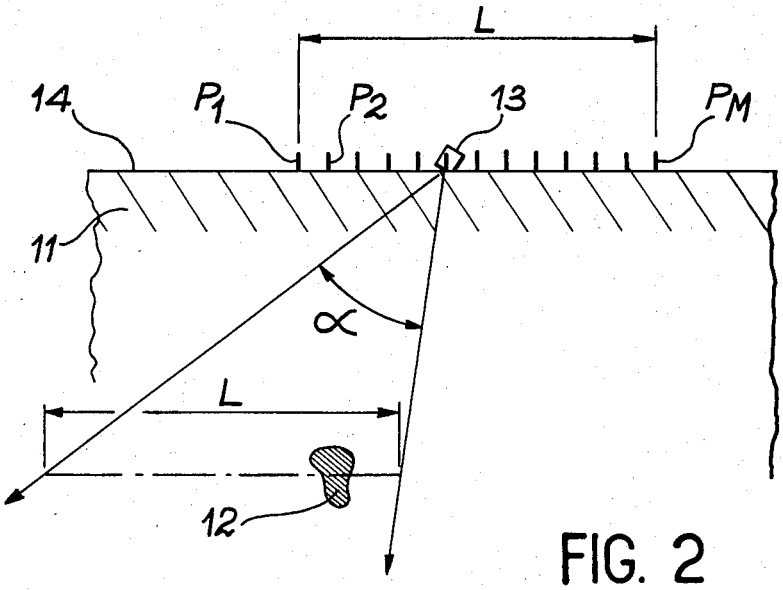
FIG. 2 a diagram explaining a known acoustic holography technique, already described.
Figure 3:
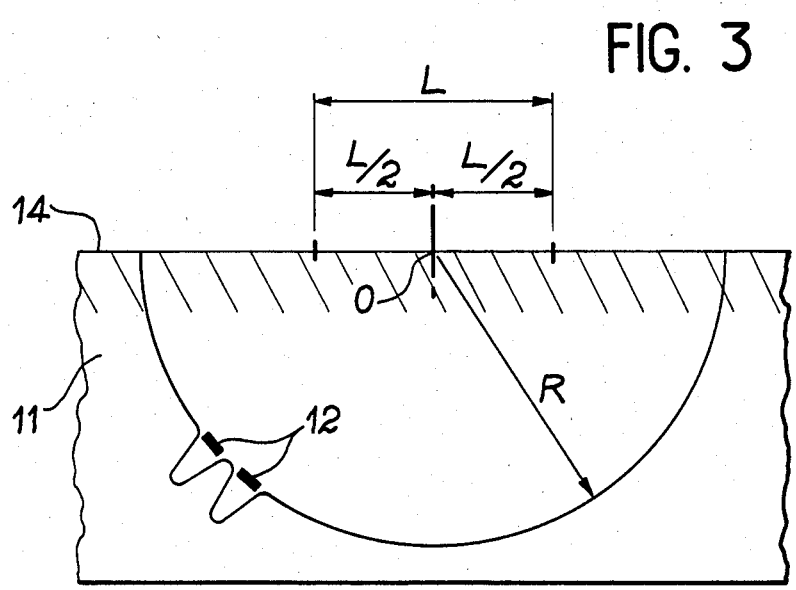
FIG. 3 an explanatory diagram of the reconstitution of faults by this known technique and already described.
Figure 4A:
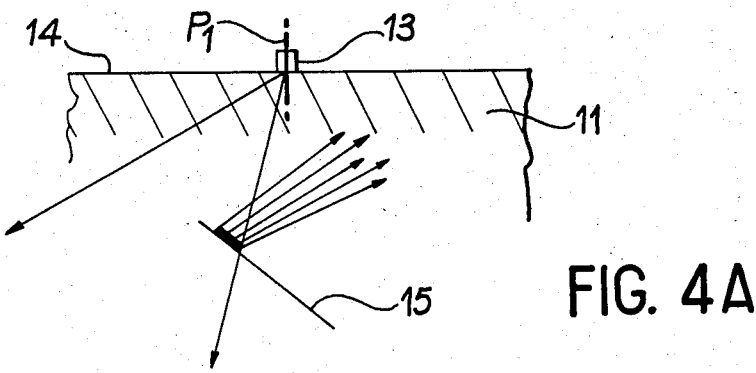
FIGS. 4A, 4B and 4C diagrammatic views showing a disadvantage of the known technique and already described.
Figure 4B:
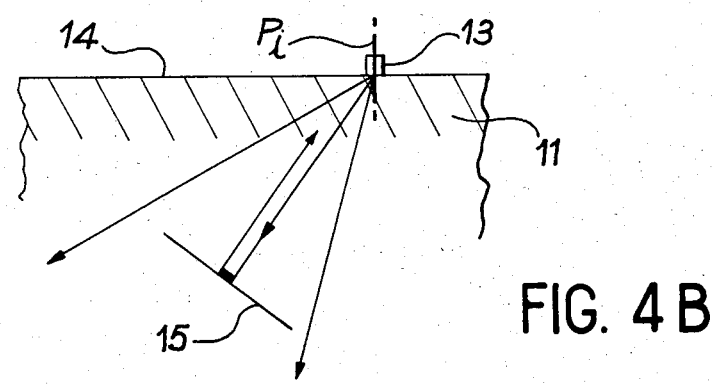
Figure 4C:
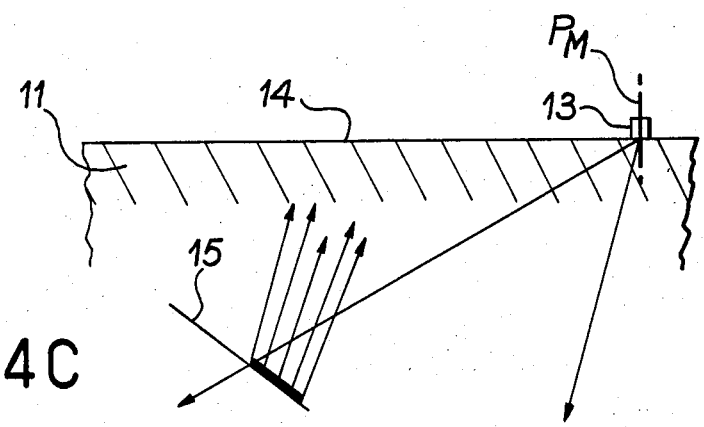

The invention makes it possible to considerably improve the signal/noise ratio compared with the apparatus and process referred to hereinbefore in connection with FIGS. 2 and 3. Thus, the acoustic intensity on the fault, for an equivalent aperture L and distance Z, is increased for holography in one plane by a factor equal to $$(D/d) \cdot L \cdot (M/L) = D \cdot M/d$$

in which M represents the number of positions successively occupied by the insonification transducer and D represents the diameter thereof. The ratio D/d represents the concentration factor linked with the convergence of the insonification transducer. The ratio L/(L/M) represents the attenuation factor linked with the fact that there are M positions on an inspection length L. Thus, the invention leads to sensitivity gains which can exceed 1000 with M at least equal to 50 and D/d at least equal to 30. In the case of three-dimensional holography, the gain is even greater and can exceed $10^6$.

Moreover, with the present invention, the orientation sensitivity is reduced compared with the aforementioned process and apparatus, because the incidence angle on a flat fault of the insonification beam does not change throughout the examination of the fault, so that detectability is maximum under these conditions.

Figure 7:
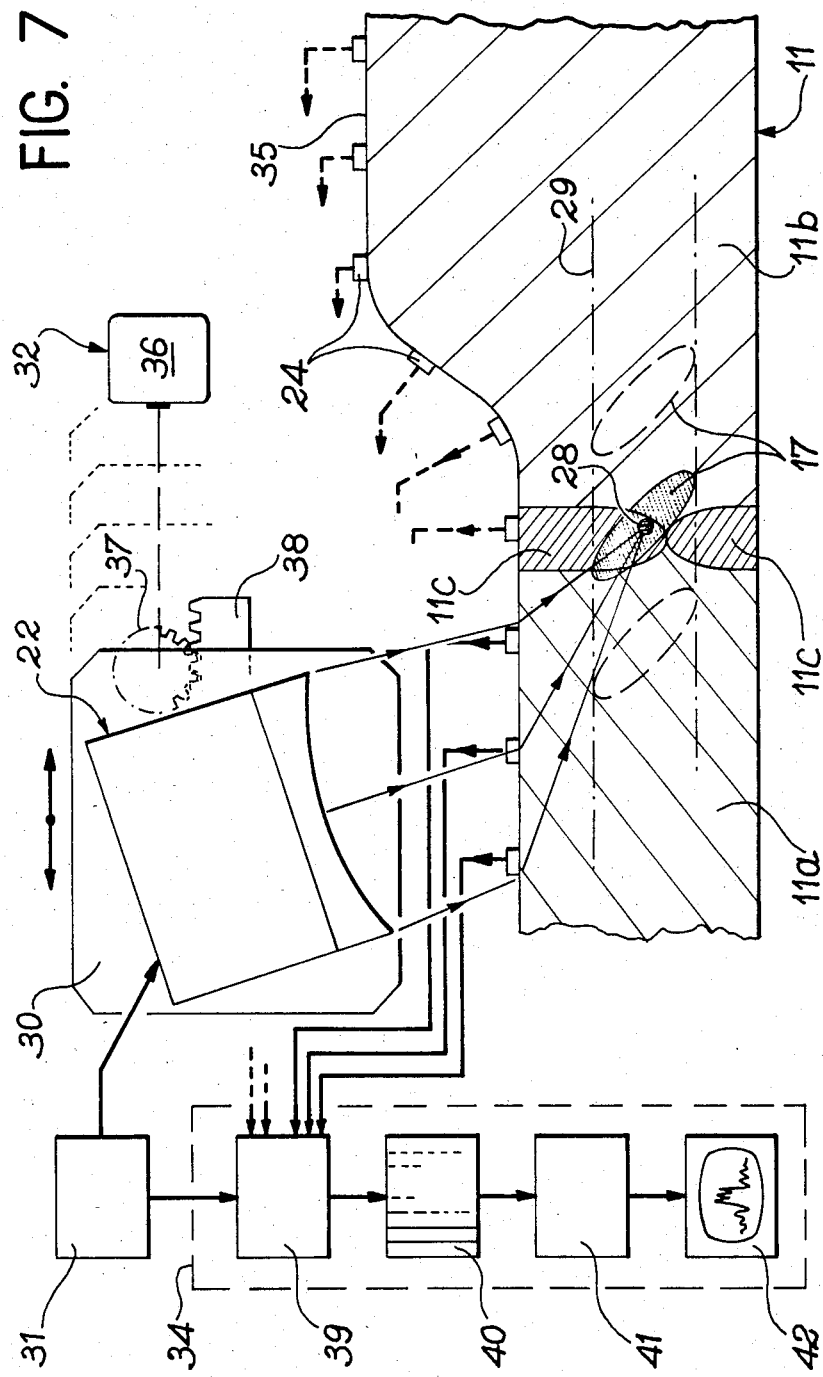
FIG. 7 a diagrammatic view of a special embodiment of the apparatus according to the invention.

FIG. 7 diagrammatically shows a special embodiment of the ultrasonic holography apparatus according to the invention. It serves to inspect a part 11 formed e.g. by two portions 11a, 11b, which are assembled to one another by a weld 11c. It is the latter which it is wished to inspect. If it has a fault or defect 28, the latter can be revealed by checking by means of the apparatus according to the invention an area 29 containing said fault. The apparatus essentially comprises a focused ultrasonic transmitter 22, mounted on a support 30 and activated by electronic control means 31; means 32 for displacing the transmitter 22; ultrasonic receivers 24; and means 34 for processing ultrasonic signals detected by the receivers.

The displacement means 32 make it possible to displace transmitter 22 by translation above the surface 35 of part 11, whereby said surface can be of a random nature. For example, the displacement means 32 comprise a stepping motor 36 controlling a pinion 37 meshing with a toothed rail 38, which is rendered rigidly integral with support 30 of transmitter 32. Receivers 24 are fixed in line on surface 35 of part 11, above the area to be inspected 29 and equidistantly with respect to one another. The number N of these receivers is determined in such a way as to eliminate any secondary image from the reconstitution of fault 28. In order to increase the signal/noise ratio, the receivers are preferably designed and oriented in such a way that their spatial reception diagram envelops the area to be inspected.

The apparatus according to the invention functions as follows. By using displacement means 32, transmitter 22 is successively positioned in M different positions located above the area to be inspected by translations of the same spacing, e.g. equal to or less than the half-width of the region insonified by the transmitter, so that the latter can successively insonify M areas 17 which, when brought together covers the area to be inspected 29. Each receiver successively receives the most M ultrasonic signals from M successively insonified areas, in response to the focused ultrasonic beam and converts these ultrasonic signals into electrical signals, which are transmitted to the processing means 34 permitting the reconstitution of the area to be inspected and consequently the fault.

These processing means 34 incorporate means 39 for determining the real and imaginary parts of the ultrasonic signals, means 40 for storing and summating these signals, (obviously represented by their real and imaginary parts), means 41 for reconstituting the area to be inspected and display means 42.

Means 39 are connected to receivers 24 and also to the receiver control means 31, so as to supply means 39 with an electronic reference signal identical to the focused beam transmitted by transmitter 22 and which is considered as a reference beam.

The storage and summation means 40 are connected to the determination means 39 and summate, for each receiver, the M successive signals corresponding thereto, thus forming N signal sums. The reconstitution means 41 connected to the storage and summation means 40 reconstitute the fault with the aid of these N sums. Finally, the display means 42, connected to the reconstitution means 41, are e.g. formed by a printer and a cathode ray tube receiver.

Figure 8:
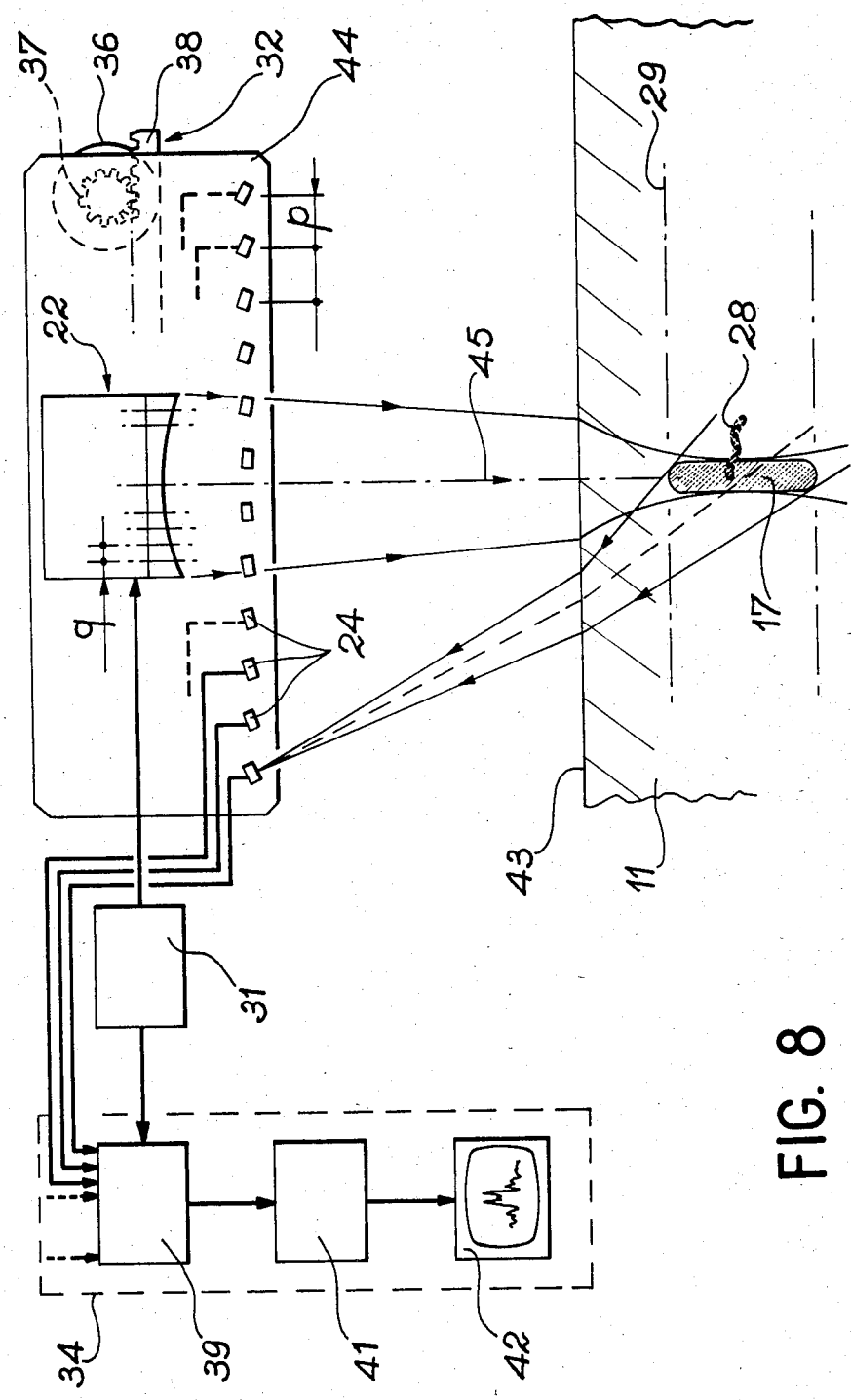
FIG. 8 a diagrammatic view of another special embodiment of the apparatus according to the invention.

FIG. 8 diagrammatically shows a special embodiment of the apparatus according to the invention making it possible to reconstitute a fault 28 present in a part 11, whereof the surface 43 is e.g. flat. The apparatus shown in FIG. 9 essentially comprises a focused ultrasonic transmitter 22, ultrasonic receivers 24 made rigidly integral with transmitter 22 via a common support 44, means 32 for displacing the transmitter (consequently the receivers), and means 34 for processing the ultrasonic signals detected by receivers 24.

As for the apparatus of FIG. 7, the displacement means 32 e.g. comprise a stepping motor 36, driving a pinion 37 which meshes with a toothed rail 38, rendered integral with the common support 44 and which makes it possible to displace this support by translation above that part of surface 43 dominating the fault 28 and parallel to said surface.

For example, transmitter 22 is fixed to support 44, in such a way that the direction 45 of the beam transmitted by it is perpendicular to surface 43. Receivers 24 are aligned on the support, equidistantly of one another with a spacing p and so as to be positioned between the transmitter and part 11. The small size of the receivers does not disturb the beam from the transmitter. For example, these receivers are substantially symmetrically distributed with respect to direction 45. In order to increase the signal/noise ratio, they are preferably oriented towards the area 17 insonified by the transmitter and are dimensioned so as to receive any information from said area 17. Obviously and as hereinbefore, the number N of these receivers is chosen so as to eliminate any secondary image from the reconstitution of the fault.

The processing means 34 are constituted in the same way as those described relative to FIG. 7, with the exception that they do not have storage and summation means 40 and in the case of the apparatus of FIG. 8, the determination means 39 are directly connected to the reconstitution means 41. In the same way transmitter 22 is connected to its control means 31, which are also connected to the determination means 39 in order to supply them with a reference electrical signal.

The operation of the apparatus of FIG. 8 is as follows. Successive translations of the transmitter are brought about by displacement means 32. These translations have the same spacing, e.g. equal to the spacing p of the receivers, and make it possible to successively position the transmitter at M different points, on the basis of which it is possible to respectively insonify M areas which, when brought together, cover the fault-containing area 29 to be inspected. For each position of the transmitter, the receivers intercept possible echoes coming from the corresponding insonified area 17 and a reconstitution of this insonified area takes place, so that the area to be inspected is progressively reconstituted in M stages.

Instead of carrying out translations of the transmitter and consequently the receivers by spacings p, it is possible to carry out the translation of the complete transmitter-receiver assembly by spacings q which are smaller than p, so as to obtain more information on the area to be inspected. For example with a spacing q equal to p/3, by displacing the assembly by three times a distance equal to p/3 from a given transmitter position, the insonification of the corresponding area does not change and everything takes place as if the transmitter was stationary and as if there were three times more receivers. In other words by using translations of spacing p/3, three times fewer receivers are required than with translations of spacing p in order to have the same amount of information.

In the description of FIGS. 7 and 8, reference has been made to a single line of receivers permitting a "linear" holography, i.e. holography in one plane (the plane of the drawing). Obviously, it would also fall within the scope of the invention to provide an apparatus incorporating several of those according to FIG. 7 or 8, whilst juxtaposing the lines of corresponding receivers, so as to carry out a "volume" examination of an object.

The invention is also applicable to the time shifted signal addition technique which is used in the SAFT method (Synthetic Aperture Focusing Technique). According to this known method, a transmitter-receiver transducer is used, said transducer emitting a short ultrasonic pulse which is focused at the surface of the sample so as to produce within said sample a large divergent beam; the same transducer used as a receiver collects the ultrasonic waves reflected by the defects of the sample, the signal being digitized and stored. The signal representing a defect is obtained by phase shifting between the signals which are collected by the receiver at neighbouring positions, and by recombining the phase shifted signals which makes it possible to improve the signal-to-noise ratio.

The application of the invention to that method consists in using a focused emission beam and a reduced number of receiver transducers which are sufficiently spaced so that the artefacts due to this reduced number can appear only outside the insonified zone and can be disregarded. According to the invention, the number of informations to be stored and processed (main disadvantage of the SAFT method) is reduced.

What is claimed is:

1. A method for the acoustic holography of an area to be inspected in an object, and for identifying faults which may exist therein, wherein said method comprises:

insonifying the area to be inspected by means of an ultrasonic transmitter producing a space-limited ultrasonic beam, displacing said transmitter so as to successively insonify M areas, in a manner which insonifies the entire area to be inspected;

detecting any ultrasonic signals coming from the successively insonified areas and producing electrical signals in response to the ultrasonic beam, by means of several ultrasonic receivers having reciprocal spacings;

determining the characteristic, by comparison to the values of a reference beam similar to said ultrasonic beam, values of the detected ultrasonic signals; and reconstructing the area to be inspected by means of said characteristic values wherein said reconstruction method comprises:

forming a main image of the fault and any possible secondary reflected images of said fault, thereof due to the said spacings, and providing a number of receivers which is predetermined in such a manner such that the distance between each secondary image and the main image exceeds the width of the areas insonified by said transmitter; and carrying out said reconstruction only in the insonified areas which have provided an ultrasonic signal, thereby eliminating any secondary images which may occur from the reconstruction of the area inspected.

2. A method according to claim 1, wherein said ultrasonic transmitter is a focused transducer.

3. An apparatus for the acoustic holographic inspection for faults of an area in an object, comprising:

an ultrasonic transmitter able to produce a space-limited ultrasonic beam and which serves to insonify the area to be inspected;

means for displacement of said transmitter enabling said transmitter to successively insonify M areas in such a manner so as to cover the area inspected;

a plurality of ultrasonic receivers having a spacing S between each of said receivers to detect any ultrasonic signals coming from said successively insonified areas in response to said ultrasonic beam; and means for processing the detected ultrasonic waves and for producing electrical signals indicative of said ultrasonic waves for determining the characteristic values of said indicative signals and for effecting a reconstruction of said area to be inspected with the aid of said characteristic values, wherein said reconstruction incorporates a main image of any faults that might exist in said area along with any possible secondary images of said faults, due to the said spacings; with the number of said receivers being predetermined in such a manner so that the distance between each secondary image produced and the main image produced exceeds the width of the areas insonified by said transmitter, and wherein said processing means serves to function in the reconstruction process only in the insonified areas which have given rise to an ultrasonic signal thereby eliminating any possible secondary images from the reconstruction of said area under inspection.

4. An apparatus according to claim 3, wherein the number of receivers is fixed as N, the displacement means serves to successively position the transmitter in M different positions, respectively corresponding to M zones, each receiver then successively receiving at the most M ultrasonic signals, with said processing means summing for each receiver, the M ultrasonic signals, thereby forming N signal sums, and wherein said processing means further comprises means for carrying out the reconstruction of said area under inspection based on the calculated N sums.

5. An apparatus according to claim 4, wherein said receivers are designed and arranged so as to have a spatial reception diagram enveloping the area to be inspected.

6. An apparatus according to claim 3, wherein the N receivers are movable and are rigidly integral with said transmitter, and wherein the displacement means serving to position the transmitter in M different positions, corresponding respectively to the M areas and further where said processing means further comprises a reconstruction means for each position of said transmitter in the area insonified.

7. An apparatus according to claim 6, wherein the displacement means comprises:

translation means, wherein said receivers are aligned in the direction of said translation and are positioned equidistant of one another in accordance with a given space p, with said displacement means having means to displace an assembly comprising the transmitter and the receivers in successive spacings that are less than the spacings between said receivers.

8. An apparatus according to claim 6, wherein said receivers are oriented such that a spatial reception diagram envelope the area insonified by said transmitter.

* * * * *